United States Patent [19]

Murdock et al.

[11] 4,226,869

[45] Oct. 7, 1980

[54] METHOD OF STIMULATING THE IMMUNE RESPONSE WITH HALOGENATED 10-(ω-DIALKYLAMINOPOLYME-THYLENEAMINO)-2-METHOX-YPYRIDO[3,2-b]QUINOLINES

[75] Inventors: Keith C. Murdock, Pearl River, N.Y.; Frederick E. Durr, Ridgewood; Martin R. Damiani, Allendale, both of N.J.; Patrick T. Izzo, Pearl River, N.Y.

[73] Assignee: American Cyanamid Company, Stamford, Conn.

[21] Appl. No.: 9,025

[22] Filed: Feb. 2, 1979

[51] Int. Cl.$^3$ .............................................. A61K 31/47
[52] U.S. Cl. ..................................................... 424/258
[58] Field of Search ......................................... 424/258

[56] References Cited

U.S. PATENT DOCUMENTS 3,931,199  1/1976  Nakanishi et al. .................. 424/258

OTHER PUBLICATIONS

Chem. Abst. 59, 13960(c) (1963)–Leduchowski et al.
Chem. Abst. 67, 20132(f) (1967)–Radzikowski et al.
Chem. Abst. 73, 35247(v) (1970)–Elslager et al.
Chem. Abst. 77, 96748(p) (1972)–Creech et al.

*Primary Examiner*—Douglas W. Robinson
*Attorney, Agent, or Firm*—Claude J. Caroli

[57] ABSTRACT

A method of stimulating the immune response in warm-blooded animals which comprises the administration of a halogenated 10-(ω-dialkylaminopolyme-thyleneamino)-2-methoxypyrido [3,2-b]quinoline.

9 Claims, No Drawings

METHOD OF STIMULATING THE IMMUNE RESPONSE WITH HALOGENATED 10-(ω-DIALKYLAMINOPOLYMETHYLENEAMINO)-2-METHOXYPYRIDO[3,2-b]QUINOLINES

BACKGROUND OF THE INVENTION

The compound 7-chloro-10-[(4-diethylamino-1-methylbutyl)amino]-2-methoxypyrido[3,2-b]quinoline is disclosed in Chemical Abstracts, 45, 8531b (1951) and Journal of the Chemical Society, 2448–2455 (1954) as an antimalarial agent. It is commercially available as the dihydrochloride salt from Aldrich Chemical Company.

SUMMARY OF THE INVENTION

This invention is concerned with a method of stimulating the immune response in a warm-blooded animal which comprises internally administering to said animal an effective immunostimulating amount of a compound of the formula:

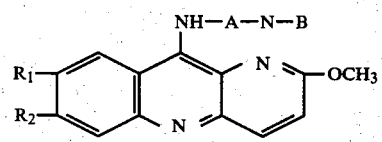

wherein $R_1$ and $R_2$ are each selected from the group consisting of hydrogen and halogen; A is a straight or branched alkyl chain of 3 to 7 carbon atoms; B is selected from the group consisting of dimethyl, diethyl and di-(2-hydroxyethyl); and the pharmaceutically acceptable salts thereof.

DESCRIPTION OF THE INVENTION

The compounds of the present invention may be prepared according to the following reaction sequence.

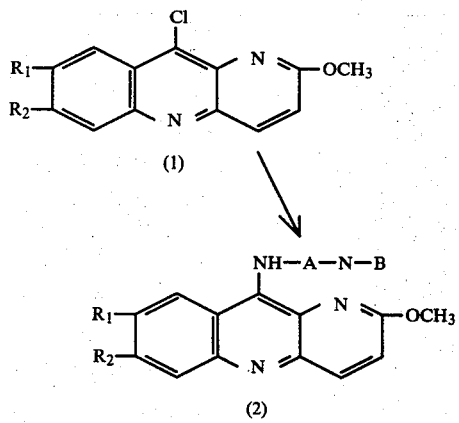

In accordance with this sequence a 10-chloro-2-methoxypyrido[3,2-b]quinoline (1) is reacted with phenol and a dialkylaminoalkylamine with heat to give compound (2) which is then diluted with ethanol and poured into a mixture of acetone and hydrochloric acid to produce the dihydrochloride.

Among the compounds contemplated by the present invention are the following:

7-Chloro-10-[(4-diethylamino-1-methylbutyl)amino]-2-methoxypyrido [3,2-b]quinoline dihydrochloride,
7-Chloro-10-[(4-diethylaminobutyl)amino]-2-methoxypyrido[3,2-b]quinoline dihydrochloride, 7-Chloro-10-[(4-dimethylaminobutyl)amino]-2-methoxypyrido[3,2-b]quinoline dihydrochloride,
7-Chloro-10-[(7-diethylaminoheptyl)amino]-2-methoxypyrido[3,2-b]quinoline dihydrochloride,
7-Chloro-10-[(6-dimethylaminohexyl)amino]-2-methoxypyrido[3,2-b]quinoline dihydrochloride,
8-Chloro-10-[4-(dimethylaminobutyl)amino]-2-methoxypyrido[3,2-b]quinoline dihydrochloride,
7-Chloro-10-[(5-diethylaminopentyl)amino]-2-methoxypyrido[3,2-b]quinoline dihydrochloride, and
2,2'-[[3-[(7-Chloro-2-methoxypyrido[3,2-b]quinolin-10-yl)amino]propyl]imino]diethanol dihydrochloride.

Immunotherapy is a new therapeutic approach to the treatment of cancer and is based on the concept that there are distinctive antigens in or on most tumor cells that distinguish them from normal host cells. A majority of tumor immunologists favor the view that potentially malignant cells constantly arise but because of their "foreignness" they are normally eliminated by a competent humoral and cellular immune system. Occasionally, however, tumor cells escape this immune surveillance and continue to reproduce—and cancer results. The reasons for the failure of the normally efficient immune surveillance mechanisms are not completely understood but it is thought that the immune system becomes less effective with increasing age. It is depressed in certain genetic immunodeficiency diseases, in various bacterial, fungal or viral infections, and in patients undergoing immunosuppressive therapy. The growth of the neoplasm itself, as well as the various therapeutic modalities designed to treat the disease, e.g., cytotoxic chemotherapy and irradiation, leads to a still greater depression of host resistance and results in an increased susceptibility to both exogenous and endogenous infections and perhaps accounts for the re-initiation of tumor growth and metastasis which all too frequently follows treatment-induced tumor remission.

If depression of the immune system facilitates the growth of malignancies, stimulation of immune responses may help the host to overcome residual cancer cells. Therefore it is considered desirable to search for chemical agents (i.e., immunostimulants) capable of restoring or stimulating the host's own immune defense mechanisms in order to overcome the deficiencies which account for the increased susceptibility to disease and failure to eradicate the cancer. It is acknowledged that such immunostimulating agents would very likely be incapable of arresting the growth of a large, rapidly proliferating tumor but that their clinical utility would derive from their capacity to enhance normal immune surveillance mechanisms in patients whose tumor burden had largely been reduced by conventional surgical, radiotherapeutic or chemotherapeutic methods. It would be hoped that the few remaining tumor cells could then be destroyed immunologically, producing a higher incidence of long term survivors or complete cures.

Experimental studies in animals have demonstrated the antitumor potential of a number of immunostimulants including live organisms of bacillus Calmette-Guerin (BCG), heat-killed cells of *Corynebacterium parvum*, polynucleotides, and the anthelmintic drug, levamisole. These substances have been shown to stimulate cellular immunity and to produce tumor regressions. Some successes have been claimed in early clinical trials with BCG against malignant melanoma and acute leukemia and with levamisole against lung cancer and breast cancer. Although the antitumor effects produced by these agents have been promising, significant therapeutic benefits have yet to be realized. Since this is a very new therapeutic approach, new drugs and methods of treatment must receive careful clinical evaluation in order to reveal the full potential of these drugs.

Modern research is directed to the discovery of a drug similar to, but more potent than, the known immunostimulants such as levamisole that would be effective in the eradication of tumor cells when used in conjunction with standard therapeutic measures. Stimulators of host resistance may be detected in animal models that can, in fact, detect both immunostimulators and anticancer agents. Mice are put in a condition simulating the immunodepression common to cancer patients. This is accomplished by infecting mice either with a leukemia virus which produces both leukemia and a disease-related immunodepression or with a transplantable mammary tumor. Effective drugs are recognized by their ability to restore or enhance the antibody response in the experimental mice.

Still another means of recognizing drug-induced stimulation of the immune response is to measure increased antibody responses or increased protective effects produced by the coadministration of vaccines and "immunoadjuvants" such as the well-known effects of Freund's adjuvant and the more recently described effects of chemicals such as levamisole. See Brugmans, J., et al., Restoration of Host Defense Mechanisms in Man by Levamisole, Life Sciences 13: 1499–1504, 1973 and Renoux, G. and Renoux, M., Stimulation of Anti-Brucella Vaccination in Mice by Tetramisole, a Phenyl-Imidothiazole Salt, Infect. & Immunity 8: 554–548, 1973.

A further discussion of the function of immune response, methods of stimulation and testing, may be found in the following references, Stimulation of Humoral and Cellular Antibody formation in Mice by Poly I:C, W. Turner, et al., Proc. Soc. Exp. Biol. & Med., 133, 334–338 (1970) and Humoral and Cellular Immune Responses in Susceptible and Resistant Strains of Mice Infected with Friend Leukemia Virus, W. S. Cezlowski, et al., Proc. Soc. Exp. Biol. & Med., 146, 619–624 (1974).

The compounds of the present invention are active as immunostimulants when tested according to the following procedures:

(A) Rauscher leukemia virus

Rauscher leukemia virus is inoculated intraperitoneally into BALB/C mice. The virus inoculum is a 20% (W/V) spleen extract made from 21-day infected spleens of BALB/C mice. All mice are within a three gram weight range, with a minimum weight of 18 g., and all mice are of the same sex, usually male. Sheep red blood cells are injected intraperitoneally on the seventh day. There are 5 mice per test group. The test compound is administered orally on the sixth day as 0.5 ml. (in 0.2% Noble agar in saline) at a dose of 37.5 to 600 mg/kg of body weight, and again on the seventh and eighth day, in the same manner. On the fourteenth day the mice are weighed and bled from the retro-orbital sinus. The blood is pooled and the harvested serum is stored at 4° C. for 24 hours. Hemagglutinin tests are performed by standard procedures using the microtiter plate technique. Acceptable hemagglutinin titer for leukemic (immunosuppressed) mice is $\leq 1:128$. Positive control compounds are Poly I:C (polyinosinic acid:-polycytidylic acid) administered intraperitoneally on days +6, +7 and +8 and/or Tilorone given orally on days +6, +7 and +8. Acceptable positive control hemaglutinin titers are 4-fold higher than the titers obtained in the leukemic control mice.

The results of this test, using representative compounds of this invention, appear in Table I.

TABLE I

| Effect of Treatment on Antibody Response to Sheep Red Blood Cells in Leukemic Mice | | | | | | | |
|---|---|---|---|---|---|---|---|
| Compound | Dose mg/kg. | Hemmagglutinin Titer* | | | | | |
| | | Test 1 | Test 2 | Test 3 | Test 4 | Test 5 | Test 6 |
| 7-Chloro-10-(4-diethylamino-1- | 600 | | 512 | | | | |
| methylbutylamino)-2-methoxypyrido | 300 | 512 | 512 | 256 | 256 | 512 | 256 |
| [3,2-b]quinoline dihydrochloride | 200 | | | 128 | 128 | | |
| | 150 | | 128 | | | 256 | 128 |
| | 100 | | | 128 | 64 | | |
| | 75 | | 64 | | | 64 | |
| | 50 | | | | 128 | | |
| | 37.5 | | 32 | | | | |
| Poly I:C | 10 | 2048 | 1024 | 512 | 512 | 1024 | 512 |
| Tilorone | 200 | 1024 | 512 | | | | |
| Non-Infected, Immunized (sheep red blood cell) Control | — | 4096 | 2048 | 1024 | 1024 | 1024 | 1024 |
| Infected, Immunized Control** | — | 64 | 32 | 64 | 64 | 128 | 64 |
| 7-Chloro-10-[(4-diethylaminobutyl) | 300 | 64 | 256 | | | | |
| amino]-2-methoxypyrido[3,2-b]quino- | 150 | 128 | 128 | | | | |
| line dihydrochloride | 75 | 128 | 128 | | | | |
| Poly I:C | 10 | 512 | 512 | | | | |
| Non-Infected, Immunized (sheep red blood cell) Control | — | 1024 | 1024 | | | | |
| Infected, Immunized Control | — | 32 | 64 | | | | |
| 7-Chloro-10-[(4-dimethylaminobutyl) | 300 | | 512 | 256 | 128 | | |
| amino]-2-methoxypyrido[3,2-b]quino- | 150 | 256 | 256 | 256 | 64 | | |
| line dihydrochloride | 75 | 64 | 64 | 128 | 64 | | |
| | 37.5 | 64 | | | | | |
| | 18.75 | 64 | | | | | |
| Poly I:C | 10 | 512 | 1024 | 512 | 512 | | |
| Non-Infected, Immunized (sheep red blood cell) Control | — | 2048 | 2048 | 1024 | 512 | | |
| Infected, Immunized Control | — | 32 | 32 | 64 | 32 | | |
| 7-Chloro-10-[(7-diethylaminoheptyl) | 300 | 256 | 512 | | | | |

TABLE I-continued

Effect of Treatment on Antibody Response to Sheep Red Blood Cells in Leukemic Mice

| Compound | Dose mg/kg. | Hemmagglutinin Titer* | | | | | |
|---|---|---|---|---|---|---|---|
| | | Test 1 | Test 2 | Test 3 | Test 4 | Test 5 | Test 6 |
| amino]-2-methoxypyrido[3,2-b] | 150 | 64 | 64 | | | | |
| quinoline dihydrochloride | 75 | 32 | | | | | |
| Poly I:C | 10 | 512 | 512 | | | | |
| Non-Infected, Imminized (sheep red blood cell) Control | — | 1024 | 1024 | | | | |
| Infected, Immunized Control | — | 32 | 64 | | | | |
| 7-Chloro-10-[(6-dimethylaminohexyl) | 300 | 128 | 128 | | | | |
| amino]-2-methoxypyrido[3,2-b] | 150 | 128 | 128 | | | | |
| quinoline dihydrochloride | 75 | 64 | 64 | | | | |
| Poly I:C | 10 | 1024 | 512 | | | | |
| Non-Infected, Immunized (sheep red blood cell) Control | — | 2048 | 1024 | | | | |
| Infected, Immunized Control | — | 32 | 32 | | | | |
| 8-Chloro-10-[(4-dimethylaminobutyl) | 300 | 256 | 256 | | | | |
| amino]-2-methoxypyrido[3,2-b]qui- | 150 | 64 | 256 | | | | |
| noline dihydrochloride | 75 | 128 | 128 | | | | |
| Poly I:C | 10 | 512 | 512 | | | | |
| Non-Infected, Immunized (sheep red blood cell) Control | — | 1024 | 1024 | | | | |
| Infected, Immunized Control | — | 64 | 64 | | | | |

*Reciprocal of serum dilution producing at least 50% agglutination of sheep red blood cells.
**Mice infected 7 days prior to injection of sheep red blood cells with Rauscher leukemia virus.

(B) Immunochemotherapy of Lewis Lung Carcinoma

The effect of immunostimulating compounds on the antitumor activity of reference cytostatic agents was demonstrated in a model in which an ineffective and toxic dose of cytoxan was given to mice bearing the Lewis lung carcinoma followed by treatment with the immunostimulant. $BDF_1$ mice were inoculated intramuscularly with $1 \times 10^5$ Lewis lung cells and treated with a single IP dose of cytoxan at 200 mg/kg three days later. Treatment with the subject compounds and known immunostimulants commenced 3 day following the cytoxan with single oral doses being given at 4 day intervals for a total of 4 doses. Test compounds (potential immunostimulants) were considered active if they provided a significant increase in long term survivors compared to the animals treated with cytoxan alone.

When 7-chloro-10-[(4-diethylamino-1-methylbutyl)amino]-2-methoxypyrido[3,2-b]quinoline dihydrochloride was administered by the oral route at 300 mg/kg following cytoxan treatment, there was a highly significant increase in long term survivors compared to the nontreated tumor group and the cytoxan-only group. The known immunomodulators pyran and poly I:C also produced increased survival times when given in combination with cytoxan. The most striking effect of 7-chloro-10-[(4-diethylamino-1-methylbutyl)amino]-2-methoxypyrido[3,2-b]quinoline dihydrochloride and the known immunomodulators was their capacity to reduce the toxicity of cytoxan in Lewis lung-bearing mice. The results of this study are recorded in Table II.

TABLE II

Immunochemotherapy of Lewis Lung Tumor in $BDF_1$ Mice

| First[1] Drug | Second[2] Drug | (mg/kg) | Route | MST | % ILS[3] | S/T |
|---|---|---|---|---|---|---|
| Placebo | Placebo | Saline | IP | 42.0 | — | 3/18 |
| Cytoxan | Placebo | Saline | IP | 14.0 | | 0/12[4] |
| Cytoxan | Pyran | 20.0 | IP | >60.0 | >329 | 11/12 |
| Cytoxan | Poly I:C | 10.0 | IP | >60.0 | >329 | 9/12 |
| Cytoxan | 7-Chloro-10-[(4-diethylamino-1-methylbutyl)amino]-2-methoxypyrido[3,2-b]quinoline dihydrochloride | 300.0 | Oral | >60.0 | >329 | 11/12 |
| Cytoxan | 7-Chloro-10-[(4-diethylamino-1-methylbutyl)amino]-2-methoxypyrido[3,2-b]quinoline dihydro- | 150.0 | Oral | 31.0 | 121 | 3/12 |

TABLE II-continued

| Immunochemotherapy of Lewis Lung Tumor in BDF$_1$ Mice | | | | | | |
|---|---|---|---|---|---|---|
| First[1] Drug | Second[2] Drug | (mg/kg) | Route | MST | % ILS[3] | S/T |
| | chloride | | | | | |

[1]Cytoxan administered to all groups, except Placebo controls, by single IP injection on day 3 at 200 mg/kg.
[2]Immune modulators administered once daily on days 6, 10, 13 and 17.
3 Percent ILS relative to cytoxan + placebo treatment group.
[4]Control for all treatment groups that received cytoxan. Cytoxan treatment at 200 mg/kg IP on day 3 resulted in premature death of tumor-bearing mice.
MST = Median Survival Time in days.
% ILS = Percent Increase in Life Span.
S/T = Survivors/Total.

(C) Adjuvant Effect on Influenzavirus Vaccine

Swiss white mice were immunized subcutaneously with 0.5 ml of an inactivated, solvent-extracted influenzavirus vaccine (A/Port Chalmers) diluted to contain 30 CCA of virus antigen. Compounds to be tested as immunoadjuvants were administered by gavage as single, daily doses on the day before, the same day, and the day after vaccination. Experimental and control mice were infected 21 days following vaccination by the intranasal instillation of 0.05 ml of a dilution of virulent influenzavirus (A/Port Chalmers) estimated to kill 50% of the non-immunized, control mice. The influence of orally administered immunoadjuvants on the protective effects of influenza vaccine was determined on the basis of differences in the extent of pulmonary disease (pneumonia) occurring in the vaccine plus drug groups compared to the vaccine-only groups.

Mice treated with 7-chloro-10-[(4-diethylamino-1-methylbutyl)amino]-2-methoxypyrido[3,2-b]quinoline dihydrochloride at the time of vaccination showed survival ratios similar to mice receiving the vaccine alone. However, among the mice surviving challenge with influenzavirus, those receiving 7-chloro-10-[(4-diethylamino-1-methylbutyl)amino]-2-methoxypyrido[3,2-b]quinoline dihydrochloride in addition to vaccine showed a lesser degree of pulmonary disease (i.e., lower lung weight/body weight ratio) than the mice receiving vaccine alone. These results are set forth in Table III. Similar studies showing potentiation of influenza vaccine with additional compounds of this invention are shown in Tables IV and V.

TABLE III

"Adjuvant" Effect on the Immunogenicity of Influenzavirus A Vaccine (Pooled Data from 3 Experiments)

| Treatment Group | Day of Treatment Relative to Infection Vaccine[1] | Drug[2] | Survivors/Total (14 Days Post-Infection) | Ratio: Lung Wt./Body Wt. |
|---|---|---|---|---|
| Vaccine Control | -21 | None | 27/30 | 1.24 |
| 7-Chloro-10-[(4-diethylamino-1-methylbutyl)amino]-2-methoxypyrido[3,2-b]quinoline dihydrochloride + vaccine | -21 | -22-21-20 | 29/30 | 1.03[3] |
| Non-Immunized, 7-Chloro-10-[(4-diethylamino-1-methylbutyl)amino]-2-methoxypyrido[3,2-b]quinoline dihydrochloride, Treated | None | -22-21-20 | 14/30 | 2.31 |
| Non-Immunized, Infected Controls | None | None | 13/30 | 1.84[4] |

[1]Influenza A/Port Chalmers, solvent-extracted vaccine - 30 CCA/mouse by subcutaneous route.
[2]Compound given by gavage at 300 mg/kg at indicated time.
[3]Significantly different from vaccine control group at P <0.05 on basis of historical data.
[4]Ratio of lung weight/body weight for noninfected, nontreated, age conditioned controls is characteristically less than 1.0 (0.65-0.80).

TABLE IV

"Adjuvant" Effect on the Immunogenicity of Influenzavirus A Vaccine

| Treatment Group | Day of Treatment Relative to Infection Vaccine[1] | Drug[2] | Survivors/Total (14 Days Post-Infection) | Ratio: Lung Wt./Body Wt. |
|---|---|---|---|---|
| Vaccine Control | -21 | None | 8/10 | 1.21 |
| 7-Chloro-10-[(7-diethylaminoheptyl)amino]-2-methoxypyrido [3,2-b]quinoline dihydrochloride + vaccine | -21 | -22-21-20 | 9/9 | 0.99[3] |
| 7-Chloro-10-[(6-di- | -21 | -22-21-20 | 10/10 | 0.88[3] |

TABLE IV-continued

"Adjuvant" Effect on the Immunogenicity of Influenzavirus A Vaccine

| Treatment Group | Day of Treatment Relative to Infection Vaccine[1] | Drug[2] | Survivors/Total (14 Days Post-Infection) | Ratio: Lung Wt./Body Wt. |
|---|---|---|---|---|
| methylaminohexyl) amino]-2-methoxy- pyrido[3,2-b]quinoline dihydrochloride + vaccine | | | | |
| Non-immunized, Infected Control | None | None | 4/10 | 1.83[4] |

[1] Influenza A/Port Chalmers, solvent-extracted vaccine - 30 CCA/mouse by subcutaneous route.
[2] Compounds given by gavage at 300 mg/kg at indicated time.
[3] Significantly different from vaccine control group at P <0.05 on basis of historical data.
[4] Ratio of lung weight/body weight for noninfected, nontreated, age conditioned controls is characteristically less than 1.0 (0.65–0.80).

TABLE V

"Adjuvant" Effect on the Immunogenicity of Influenzavirus A Vaccine

| Treatment Group | Day of Treatment Relative to Infection Vaccine[1] | Drug[2] | Survivors/Total (14 Days Post-Infection) | Ratio: Lung Wt./Body Wt. |
|---|---|---|---|---|
| Vaccine Control | -21 | None | 10/10 | 1.33 |
| 7-Chloro-10-[5-di- ethylaminopentyl) amino]-2-methoxypy- rido[3,2-b]quinoline dihydrochloride + vaccine | -21 | -22-21-20 | 10/10 | 1.12[3] |
| 2,2'-[[3-[(7-Chloro- 2-methoxypyrido[3,2-b] quinolin-10-yl)amino] propyl]imino]diethanol dihydrochloride + vaccine | -21 | -22-21-20 | 9/10 | 1.03[3] |
| 7-Chloro-10-[(4-di- ethylamino-1-methyl- butyl)amino]-2-methoxy- pyrido[3,2-b]quinoline dihydrochloride + vaccine | -21 | -22-21-20 | 10/10 | 0.97[3] |
| Non-Immunized, 7- Chloro-10-[(4-diethyl- amino-1-methylbutyl)amino]- 2-methoxypyrido[3,2-b]qui- noline dihydrochloride, Treated | None | -22-21-20 | 7/10 | 1.76 |
| Non-Immunized, Infected Controls | None | None | 6/10 | 2.41[4] |

[1] Influenza A/Port Chalmers, solvent-extracted vaccine - 30 CCA/mouse by subcutaneous route.
[2] Compounds given by gavage at 300 mg/kg at indicated time.
[3] Significantly different from vaccine control group at P <0.05 on basis of historical data.
[4] Ratio of lung weight/body weight for noninfected, nontreated, age conditioned controls is characteristically less than 1.0 (0.65–0.80).

The compounds of the present invention are active orally as immunostimulants. A range of doses may be employed depending on the mode of administration. For oral administration, these compounds are usually administered at from about 37.5 to about 600 mg./kg./day.

In therapeutic use, the compounds of this invention may be administered in the form of conventional pharmaceutical compositions. Such compositions may be formulated so as to be suitable for oral administration. The active ingredient may be combined in admixture with a pharmaceutically acceptable carrier, which carrier may take a wide variety of forms, depending on the form or preparation desired for administration. These compounds can be used on compositions such as tablets. Here, the principal active ingredient is mixed with conventional tabletting ingredients such as corn starch, lactose, sucrose, sorbitol, talc, stearic acid, magnesium stearate, dicalcium phosphate, gums or similar materials such as non-toxic pharmaceutically acceptable diluents or carriers. The tablets or pills of these novel compositions can be laminated or otherwise compounded to provide a dosage from affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene- maleic acid copolymer together with known materials contributing to the enteric properties of the coating. The tablet or pill may be colored through the use of an appropriate non-toxic dye.

The liquid forms in which the novel compositions of the present invention may be incorporated for administration include suitable flavored suspensions, elixirs, emulsions, solutions and similar pharmaceutical vehicles.

These dosage forms refer to physically discrete units suitable as unitary dosage for warm-blooded animals, each unit containing a predetermined quantity of active component calculated to produce the desired therapeutic effect in association with the required pharmaceutical diluent, carrier or vehicle. The specification for the novel dosage forms of this invention are indicated by characteristics of the active component. Examples of suitable dosage forms are tablets, capsules, pills, powder packets, granules, wafers, cachets, teaspoonfuls, dropperfuls, segregated multiples of any of the foregoing and other forms as herein described.

EXAMPLE 1

7-Chloro-10-[(4-diethylamino-1-methylbutyl)amino]-2-methoxypyrido[3,2-b]quinoline dihydrochloride This compound may be prepared as described in Chemical Abstracts, 45, 8531b (1951) or as described by Besley, D. M. and Goldberg, A. A. in J. Chem. Soc., 2448-2455, (1954) or it may be purchased from Aldrich Chemical Co.

EXAMPLE 2

7-Chloro-10-[(4-diethylaminobutyl)amino]-2-methoxypyrido[3,2-b]quinoline dihydrochloride A mixture of 2.8 g. of 7,10-dichloro-2-methoxypyrido[3,2-b]quinoline, 1.5 g. of 4-diethylaminobutylamine and 6.5 g. of phenol is heated at 100° C. for 3 hours. The reaction is cooled, 20 ml. of ethanol is added and this mixture is poured into a mixture of 200 ml. of acetone and 2.5 ml. of concentrated hydrochloric acid. The yellow solic is collected, air-dried and recrystallized from ethanol, giving the desired product, mp. 246°-274° C. (dec.).

EXAMPLE 3

7-Chloro-10-[(4-dimethylaminobutyl)amino]-2-methoxypyrido[3,2-b]quinoline dihydrochloride A mixture of 4.2 g. of 7,10-dichloro-2-methoxypyrido[3,2-b]quinoline, 1.6 g. of dimethylaminobutylamine and 10 g. of phenol is stirred and heated on a steam bath for 3 hours. The reaction is cooled, 30 ml. of ethanol is added and this mixture is poured into a mixture of 300 ml. of acetone and 3.75 ml. of concentrated hydrochloric acid. The yellow precipitate is collected, washed with acetone, air-dried and recrystallized from 100 ml. of 95% alcohol giving the desired product as yellow crystals, mp. 237°-238° C. (dec.)

EXAMPLE 4

7-Chloro-10-[(7-diethylaminoheptyl)amino]-2-methoxypyrido[3,2-b]quinoline dihydrochloride A mixture of 2.8 g. of 7,10-dichloro-2-methoxypyrido[3,2-b]quinoline, 2.0 g. of 7-diethylaminoheptylamine and 6.5 g. of phenol is stirred on a steam bath for 3 hours. The reaction is cooled, 20 ml. of 95% alcohol is added and this mixture is poured into a mixture of 200 ml. of acetone and 2.5 ml. of concentrated hydrochloric acid. The resulting solution is cooled in ice. The solid is collected and recrystallized from n-propanol:ethyl acetate (50:50), giving the desired product as yellow crystals, mp. 170°-174° C. (dec.).

EXAMPLE 5

7-Chloro-10-[(6-dimethylaminohexyl)amino]-2-methoxypyrido[3,2-b]quinoline dihydrochloride A mixture of 2.8 g. of 7,10-dichloro-2-methoxypyrido[3,2-b]quinoline, 1.5 g. of dimethylaminohexylamine and 6.5 g. of phenol is stirred and heated on a steam bath for 3 hours. The mixture is cooled, 20 ml. of ethanol are added and the dark solution is poured into a mixture of 200 ml. of acetone and 2.5 ml. of concentrated hydrochloric acid. The mixture is cooled in ice. The solid is collected, air-dried and recrystallized from 3A alcohol:acetone (50:50), giving the desired product as yellow crystals, mp. 243°-244° C. (dec.).

EXAMPLE 6

8-Chloro-10-[(4-dimethylaminobutyl)amino]-2-methoxypyrido[3,2-b]quinoline dihydrochloride To a solution of 19.1 g. of 2,5-dichlorobenzoic acid [Besley & Goldberg, J. Chem. Soc., 2448 (1954)] in 100 ml. of amyl alcohol is added 6.9 g. of anhydrous potassium carbonate and 0.1 g. of copper oxide. The mixture is stirred and heated at 100° C. for 30 minutes, then 13.0 g. of 5-amino-2-methoxypyridine is added and the mixture is heated at reflux and stirred for 3 hours. A small amount of water forms and is collected in a Dean-Stark apparatus. The reaction mixture is cooled, poured into water and made basic with potassium carbonate. The mixture is steam-distilled to remove the amyl alcohol, then filtered and the filtrate is acidified to pH 6. The mixture is again filtered and this pink filtrate is acidified with 6 N hydrochloric acid to pH 4. The solid is collected, giving 5-chloro-2-(6-methoxy-3-pyridylamino)-benzoic acid as a pink crystalline solid.

A mixture of 8.4 g. of the above product and 60 ml. of phosphoryl chloride is heated under reflux for 5½ hours. The excess phosphoryl chloride is removed in vacuo and the solid residue is broken up in a mixture of 250 g. of ice and 70 ml. of concentrated ammonium hydroxide. The mixture is maintained in an ice bath, with stirring, for 6 hours. The solid is collected, slurried in acetone, filtered, dried and recrystallized from boiling dimethylformamide, giving 8,10-dichloro-2-methoxybenzo[b]-1,5-naphthyridine as pale green crystals.

A mixture of 2.8 g. of the preceding compound, 1.3 g. of dimethylaminobutylamine and 6.5 g. of phenol is stirred and heated on a steam bath for 4 hours. The reaction is cooled, 20 ml. of 3A alcohol is added and this solution is poured into a solution of 2.5 ml. of concentrated hydrochloric acid and 200 ml. of acetone. The solid is collected and recrystallized from 3A alcohol, giving the desired product as yellow crystals, mp. 251°-252° C. (dec.)

EXAMPLE 7

7-Chloro-10-[(5-diethylaminopentyl)amino]-2-methoxypyrido[3,2-b]quinoline dihydrochloride A mixture of 2.8 g. of 7,10-dichloro-2-methoxypyrido[3,2-b]quinoline, 1.7 g. of 5-diethylaminopentylamine and 6.5 g. of phenol was treated as in Example 5 to obtain the title compound, m.p. 232°-233° C.

EXAMPLE 8

2,2'-[[3-[(7-Chloro-2-methoxypyrido[3,2-b]quinolin-10-yl)amino]propyl]imino]diethanol dihydrochloride A mixture of 2.8 g. of 7,10-dichloro-2-methoxypyrido [3,2-b]quinoline, 1.8 g. of 3-[bis(2-hydroxyethyl)amino]-propylamine and 6.5 g. of phenol was treated as in Example 5 to obtain the title compound, m.p. 243°–245° C.

EXAMPLE 9

Preparation of Compressed Tablet

| Ingredient | mg./Tablet |
| --- | --- |
| Active compound | 5–500 |
| Dibasic calcium phosphate N. F. | qs |
| Starch U.S.P. | 40 |
| Modified starch | 10 |
| Magnesium stearate U.S.P. | 1–5 |

EXAMPLE 10

Preparation of Hard Shell Capsule

| Ingredient | mg./Capsule |
| --- | --- |
| Active compound | 5–500 |
| Lactose, spray dried | qs |
| Magnesium stearate | 1–10 |

EXAMPLE 11

Preparation of Oral Liquid

| Ingredient | % W/V |
| --- | --- |
| Active compound | 0.5–5 |
| Liquid sugar | 75.0 |
| Methyl paraben U.S.P. | 0.18 |
| Propyl paraben U.S.P. | 0.02 |
| Flavoring agent | qs |
| Purified water    qs ad | 100.0 |

We claim:

1. A method of stimulating the immune response in a warm-blooded animal which comprises orally administering to said animal an effective immunostimulating amount of a compound of the formula:

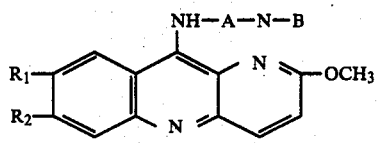

wherein $R_1$ and $R_2$ are each selected from the group consisting of hydrogen and halogen; A is a straight or branched alkyl chain of 3 to 7 carbon atoms; B is selected from the group consisting of dimethyl, diethyl and di-(2-hydroxyethyl); and the pharmaceutically acceptable salts thereof.

2. A method according to claim 1, wherein the compound is 7-chloro-10-[(4-diethylamino-1-methylbutyl)amino]-2-methoxypyrido[3,2-b]quinoline dihydrochloride.

3. A method according to claim 1, wherein the compound is 7-chloro-10-[(4-diethylaminobutyl)amino]-2-methoxypyrido[3,2-b]quinoline dihydrochloride.

4. A method according to claim 1, wherein the compound is 7-chloro-10-[(4-dimethylaminobutyl)amino]-2-methoxypyrido [3,2-b]quinoline dihydrochloride.

5. A method according to claim 1, wherein the compound is 7-chloro-10-[(7-diethylaminoheptyl)amino]-2-methoxypyrido [3,2-b]quinoline dihydrochloride.

6. A method according to claim 1, wherein the compound is 7-chloro-10-[(6-dimethylaminohexyl)amino]-2-methoxypyrido[3,2-b]quinoline dihydrochloride.

7. A method according to claim 1, wherein the compound is 8-chloro-10-[(4-dimethylaminobutyl)amino]-2-methoxypyrido[3,2-b]quinoline dihydrochloride.

8. A method according to claim 1, wherein the compound is 7-chloro-10-[(5-diethylaminopentyl)amino]-2-methoxypyrido[3,2-b]quinoline dihydrochloride.

9. A method according to claim 1, wherein the compound is 2,2'-[[3-[(7-chloro-2-methoxypyrido[3,2-b]quinolin-10-yl)amino]propyl]imino]diethanol dihydrochloride.

* * * * *